US009878158B2

(12) United States Patent
Hershey et al.

(10) Patent No.: US 9,878,158 B2
(45) Date of Patent: *Jan. 30, 2018

(54) NEUROMODULATION SYSTEM AND METHOD FOR REDUCING ENERGY REQUIREMENTS USING FEEDBACK

(71) Applicant: Boston Scientific Neuromodulation Corporation, Valencia, CA (US)

(72) Inventors: Bradley Lawrence Hershey, Valencia, CA (US); Kerry Bradley, Glendale, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/299,142

(22) Filed: Oct. 20, 2016

(65) Prior Publication Data

US 2017/0036024 A1    Feb. 9, 2017

Related U.S. Application Data

(60) Continuation of application No. 14/800,183, filed on Jul. 15, 2015, now Pat. No. 9,480,841, which is a (Continued)

(51) Int. Cl.
*A61N 1/00* (2006.01)
*A61N 1/36* (2006.01)
(Continued)

(52) U.S. Cl.
CPC ........ *A61N 1/36071* (2013.01); *A61B 5/4833* (2013.01); *A61N 1/0551* (2013.01);
(Continued)

(58) Field of Classification Search
CPC ............ A61N 1/37211; A61N 1/36128; A61N 1/36071; A61N 1/36139; A61B 5/4833;
(Continued)

(56) References Cited

U.S. PATENT DOCUMENTS 6,516,227 B1    2/2003   Meadows et al.
6,895,280 B2    5/2005   Meadows et al.
(Continued)

OTHER PUBLICATIONS

"U.S. Appl. No. 13/930,176, Corrected Notice of Allowance dated Apr. 29, 2015", 4 pgs.
(Continued)

*Primary Examiner* — Robert N Wieland
(74) *Attorney, Agent, or Firm* — Schwegman Lundberg & Woessner, P.A.

(57) ABSTRACT

An electrical neuromodulation system and method of meeting a therapeutic goal for a patient using a neuromodulation device. A modulation parameter value is varied by a step size. The neurostimulation device instructs the neuromodulation device to deliver electrical energy to at least one electrode in accordance with the varied modulation parameter value. A therapeutic feedback indicator is compared to a threshold in response to the delivery of the electrical energy. Whether the therapeutic goal has been met is determined based on the comparison, and the previous steps are repeated to determine the modulation parameter value at the resolution of the step size that minimizes energy consumption of the neuromodulation device required to meet the therapeutic goal when delivering the electrical energy to the electrode(s) in accordance with the varied modulation parameter value.

20 Claims, 8 Drawing Sheets

Related U.S. Application Data division of application No. 13/930,176, filed on Jun. 28, 2013, now Pat. No. 9,084,900.

(60) Provisional application No. 61/666,605, filed on Jun. 29, 2012.

(51) Int. Cl.
*A61N 1/372* (2006.01)
*A61N 1/05* (2006.01)
*A61B 5/00* (2006.01)

(52) U.S. Cl.
CPC ..... *A61N 1/36128* (2013.01); *A61N 1/36132* (2013.01); *A61N 1/36135* (2013.01); *A61N 1/36171* (2013.01); *A61N 1/37211* (2013.01); *A61B 2560/0209* (2013.01)

(58) Field of Classification Search
CPC ........ A61B 2560/0209; A61B 5/04001; A61B 5/4836
See application file for complete search history.

(56) References Cited

U.S. PATENT DOCUMENTS

| | | | |
|---|---|---|---|
| 6,993,384 | B2 | 1/2006 | Bradley et al. |
| 7,539,538 | B2 | 5/2009 | Parramon et al. |
| 9,084,900 | B2 | 7/2015 | Hershey et al. |
| 9,480,841 | B2 | 11/2016 | Hershey et al. |
| 2003/0139781 | A1 | 7/2003 | Bradley et al. |
| 2005/0267546 | A1 | 12/2005 | Parramon et al. |
| 2010/0137938 | A1 | 6/2010 | Kishawi et al. |
| 2012/0303090 | A1 | 11/2012 | Wolf, II |
| 2013/0231721 | A1 | 9/2013 | Decharms |
| 2013/0304152 | A1 | 11/2013 | Bradley et al. |
| 2014/0005744 | A1 | 1/2014 | Hershey et al. |
| 2014/0039578 | A1 | 2/2014 | Whitehurst et al. |
| 2014/0180359 | A1* | 6/2014 | Walker ................ A61N 1/0551 607/46 |
| 2014/0236257 | A1 | 8/2014 | Parker et al. |
| 2016/0008600 | A1 | 1/2016 | Hershey et al. |

OTHER PUBLICATIONS

"U.S. Appl. No. 13/930,176, Non Final Office Action dated Nov. 24, 2014", 14 pgs.
"U.S. Appl. No. 13/930,176, Notice of Allowance dated Mar. 17, 2015", 7 pgs.
"U.S. Appl. No. 13/930,176, Preliminary Amendment filed Jun. 28, 2013", 5 pgs.
"U.S. Appl. No. 13/930,176, Response filed Feb. 23, 2015 to Non Final Office Action dated Nov. 24, 2014", 8 pgs.
"U.S. Appl. No. 14/800,183, Non Final Office Action dated Mar. 3, 2016", 8 pgs.
"U.S. Appl. No. 14/800,183, Notice of Allowance dated Jun. 29, 2016", 7 pgs.
"U.S. Appl. No. 14/800,183, Preliminary Amendment filed Jul. 15, 2015", 5 pgs.
"U.S. Appl. No. 14/800,183, Response filed May 31, 2016 to to Non Final Office Action dated Mar. 3, 2016", 8 pgs.

* cited by examiner

NEUROMODULATION SYSTEM AND METHOD FOR REDUCING ENERGY REQUIREMENTS USING FEEDBACK

RELATED APPLICATION DATA

The present application is a continuation of U.S. application Ser. No. 14/800,183, filed Jul. 15, 2015, now issued as U.S. Pat. No. 9,480,841, which is a divisional of U.S. application Ser. No. 13/930,176, filed Jun. 28, 2013, now issued as U.S. Pat. No. 9,084,900, which claims the benefit under 35 U.S.C. § 119 to U.S. provisional patent application Ser. No. 61/666,605, filed Jun. 29, 2012. The foregoing applications are hereby incorporated by reference into the present application in their entirety.

FIELD OF THE INVENTION

The present inventions relate to tissue modulation systems, and more particularly, to systems and methods for adjusting the modulation provided to tissue to minimize the energy requirements of the systems.

BACKGROUND OF THE INVENTION

Implantable neuromodulation systems have proven therapeutic in a wide variety of diseases and disorders. Pacemakers and Implantable Cardiac Defibrillators (ICDs) have proven highly effective in the treatment of a number of cardiac conditions (e.g., arrhythmias Spinal Cord Stimulation (SCS) systems have long been accepted as a therapeutic modality for the treatment of chronic pain syndromes, and the application of spinal modulation has begun to expand to additional applications, such as angina pectoris and incontinence. Deep Brain Stimulation (DBS) has also been applied therapeutically for well over a decade for the treatment of refractory Parkinson's Disease, and DBS has also recently been applied in additional areas, such as essential tremor and epilepsy. Further, in recent investigations, Peripheral Nerve Stimulation (PNS) systems have demonstrated efficacy in the treatment of chronic pain syndromes and incontinence, and a number of additional applications are currently under investigation. Furthermore, Functional Electrical Stimulation (FES) systems such as the Freehand system by NeuroControl (Cleveland, Ohio) have been applied to restore some functionality to paralyzed extremities in spinal cord injury patients.

Each of these implantable neuromodulation systems typically includes one or more electrode carrying modulation leads, which are implanted at the desired stimulation site, and a neuromodulation device implanted remotely from the stimulation site, but coupled either directly to the modulation lead(s) or indirectly to the modulation lead(s) via a lead extension. Thus, electrical pulses can be delivered from the neuromodulation device to the electrode(s) to activate a volume of tissue in accordance with a set of modulation parameters and provide the desired efficacious therapy to the patient. In particular, electrical energy conveyed between at least one cathodic electrode and at least one anodic electrode creates an electrical field, which when strong enough, depolarizes (or "stimulates") the neurons beyond a threshold level, thereby inducing the firing of action potentials (APs) that propagate along the neural fibers. A typical modulation parameter set may include the electrodes that are sourcing (anodes) or returning (cathodes) the modulating current at any given time, as well as the amplitude, duration, and rate of the stimulation pulses.

The neuromodulation system may further comprise a handheld patient programmer to remotely instruct the neuromodulation device to generate electrical stimulation pulses in accordance with selected modulation parameters. The handheld programmer in the form of a remote control (RC) may, itself, be programmed by a clinician, for example, by using a clinician's programmer (CP), which typically includes a general purpose computer, such as a laptop, with a programming software package installed thereon.

Of course, neuromodulation devices are active devices requiring energy for operation, and thus, the neuromodulation system may oftentimes includes an external charger to recharge a neuromodulation device, so that a surgical procedure to replace a power depleted neuromodulation device can be avoided. To wirelessly convey energy between the external charger and the implanted neuromodulation device, the charger typically includes an alternating current (AC) charging coil that supplies energy to a similar charging coil located in or on the neuromodulation device. The energy received by the charging coil located on the neuromodulation device can then be used to directly power the electronic componentry contained within the neuromodulation device, or can be stored in a rechargeable battery within the neurotnodulation device, which can then be used to power the electronic componentry on-demand.

Typically, the therapeutic effect for any given neurotnodulation application may be optimized by adjusting the modulation parameters. Often, these therapeutic effects are correlated to the diameter of the nerve fibers that innervate the volume of tissue to be modulated. For example, in SCS, activation (i.e., recruitment) of large diameter sensory fibers is believed to reduce/block transmission of smaller diameter pain fibers via interneuronal interaction in the dorsal horn of the spinal cord. Activation of large sensory fibers also typically creates a sensation known as paresthesia that can be characterized as an alternative sensation that replaces the pain signals sensed by the patient.

Although alternative or artifactual sensations are usually tolerated relative to the sensation of pain, patients sometimes report these sensations to be uncomfortable, and therefore, they can be considered an adverse side-effect to neuromodulation therapy in some cases. It has been shown that high-frequency pulsed electrical energy can be effective in providing neuromodulation therapy for chronic pain without causing paresthesia. In contrast to conventional neuromodulation therapies, which employ low- to mid-frequencies to provide a one-to-one correspondence between the generation of an AP and each electrical pulse, high frequency modulation (e.g., 1 KHz 50 KHz) can be employed to block naturally occurring APs within neural fibers or otherwise disrupt the APs within the neural fibers. Although high-frequency modulation therapies have shown good efficacy in early studies, one notable drawback is the relatively high energy requirement to achieve high-frequency modulation in contrast to low- to mid-frequency modulation. In particular, the amount of energy required to generate an electrical waveform is proportional to the frequency of the electrical waveform. Thus, neuromodulation devices that generate relatively low frequency modulation energy typically need to be recharged only once every 1-2 weeks, whereas neuromodulation devices that generate relatively high frequency modulation energy may require a daily or more frequent recharge.

There, thus, remains a need to decrease the energy requirements for high-frequency neuromodulation therapy.

SUMMARY OF THE INVENTION

In accordance with a first aspect of the present inventions, an electrical neuromodulation system is provided. The system comprises a neuromodulation device capable of outputting electrical energy (which may be pulsed) to at least one electrode in accordance with a modulation parameter value. The frequency of the electrical energy may be relatively high (e.g., 1 KHz-50 KHz). The modulation parameter may be a pulse rate, or may be other parameters, such as pulse amplitude, pulse width, duty cycle, and electrode combination. The system further comprises memory configured for storing a threshold indicative of a therapeutic goal (e.g., the alleviation of chronic pain).

The system further comprises control/processing circuitry configured for automatically (a) varying the modulation parameter value by a step size, (b) instructing the neuromodulation device to output the electrical energy to the electrode(s) in accordance with the varied modulation parameter value, (c) comparing a therapeutic feedback indicator to the stored threshold in response to the delivery of the electrical energy, and (d) determining whether the therapeutic goal has been met based on the comparison. The therapeutic feedback indicator may be conscious feedback from the patient. In an alternative embodiment, the system further comprises at least one sensor configured for sensing a therapeutic feedback indicator, e.g., a body activity, body temperature, blood flow, electrocardiogram and derived autonomic tone metrics thereof, electrocortigram, electroencephalogram, tissue or transcutaneous oxygen tension, glucose concentration, electrode impedance, compound action potentials, intra- or extra-cellular potential or electrical current, or chemical species concentration.

The control/processing circuitry is further configured for repeating steps (a)-(d) to determine the modulation parameter value at the resolution of the step size that minimizes energy consumption of the neuromodulation device required to meet the therapeutic goal when delivering the electrical energy to the electrode(s) in accordance with the varied modulation parameter value. This determination may be accomplished in any one of a variety of manners.

For example, in one embodiment, the controller/processor is configured for incrementally varying the modulation parameter value at step (a) to increase the energy consumption of the neuromodulation device, and if the therapeutic goal is initially determined to not be met at step (d), repeating steps (a)-(d) until the therapeutic goal has been determined to be met at step (d), such that the modulation parameter value that minimizes energy consumption of the neuromodulation device required to meet the therapeutic goal is determined to be the last modulation parameter value. In another embodiment, the controller/processor is configured for incrementally varying the modulation parameter value at step (a) to decrease the energy consumption of the neuromodulation device, and if the therapeutic goal is initially determined to be met at step (d), repeating steps (a)-(d) until the therapeutic goal has been determined to not be met at step (d), such that the modulation parameter value that minimizes energy consumption of the neuromodulation device required to meet the therapeutic goal is determined to be the previous modulation parameter value.

The memory and control/processing circuitry may be contained in the neuromodulation device or an external control device. In an optional embodiment, the system further comprises a battery configured for storing power used to generate the electrical energy.

In accordance with a second aspect of the present inventions, a method of meeting a therapeutic goal (e.g., alleviating chronic pain) for a patient using a neuromodulation device is provided. The method comprises (a) incrementally varying a modulation parameter value by a step size. The modulation parameter may be a pulse rate, or may be other parameters, such as pulse amplitude, pulse width, duty cycle, and electrode combination. The method further comprises (h) delivering electrical energy (which may be pulsed) from the neuromodulation device to at least one electrode (which may be implanted within the patient) adjacent a target tissue site in accordance with the varied modulation parameter value, thereby modulating (e.g., stimulating) the target tissue site. The frequency of the electrical energy may be relatively high (e.g., 1 KHz-50 KHz).

The method further comprises (c) analyzing a therapeutic feedback indicator in response to the modulation of the target tissue site by the delivered electrical energy. The therapeutic feedback indicator may be conscious feedback from the patient. Alternatively, the therapeutic feedback indicator may be, e.g., a body activity, body temperature, blood flow, electrocardiogram and derived autonomic tone metrics thereof, electrocortigram, electroencephalogram, tissue or transcutaneous oxygen tension, glucose concentration, electrode impedance, compound action potentials, intra- or extra-cellular potential or electrical current, or chemical species concentration.

The method further comprises determining whether the therapeutic goal has been met based on the analyzed therapeutic feedback indicator. For example, the therapeutic feedback indicator may be compared to a threshold indicative of the therapeutic goal, and determining whether the therapeutic goal had been met may be based on the comparison.

The method further comprises (e) repeating steps (a)-(d) to determine the modulation parameter value at the resolution of the step size that minimizes energy consumption of the neuromodulation device required to meet the therapeutic goal when delivering the electrical energy to the electrode(s) in accordance with the varied modulation parameter value. This determination may be accomplished in any one of a variety of manners.

For example, in one method, the modulation parameter value is incrementally varied at step (a) to increase the energy consumption of the neuromodulation device, the therapeutic goal is initially determined to not be met at step (d), and steps (a)-(d) are repeated until the therapeutic goal has been determined to be met at step (d), such that the modulation parameter value that minimizes energy consumption of the neuromodulation device required to meet the therapeutic goal is determined to be the last modulation parameter value. In another method, the modulation parameter value is incrementally varied at step (a) to decrease the energy consumption of the neuromodulation device, the therapeutic goal is initially determined to be met at step (d), and steps (a)-(d) are repeated until the therapeutic goal has been determined to not be met at step (d), such that the modulation parameter value that minimizes energy consumption of the neuromodulation device required to meet the therapeutic goal is determined to be the previous modulation parameter value.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE EMBODIMENTS

The description that follows relates to a spinal column modulation (SCM) system. However, it is to be understood that the while the invention lends itself well to applications in SCM, the invention, in its broadest aspects, may not be so limited. Rather, the invention may be used with any type of implantable electrical circuitry used to modulate tissue. For example, the present invention may be used as part of a pacemaker, a defibrillator, a cochlear modulator device, a retinal modulator device, a modulator device configured to produce coordinated limb movement, a cortical modulator device, a deep brain modulator device, peripheral nerve modulator device, micromodulator device, or in any other tissue modulator device configured to treat urinary incontinence, sleep apnea, shoulder sublaxation, headache, etc.

Figure 1:
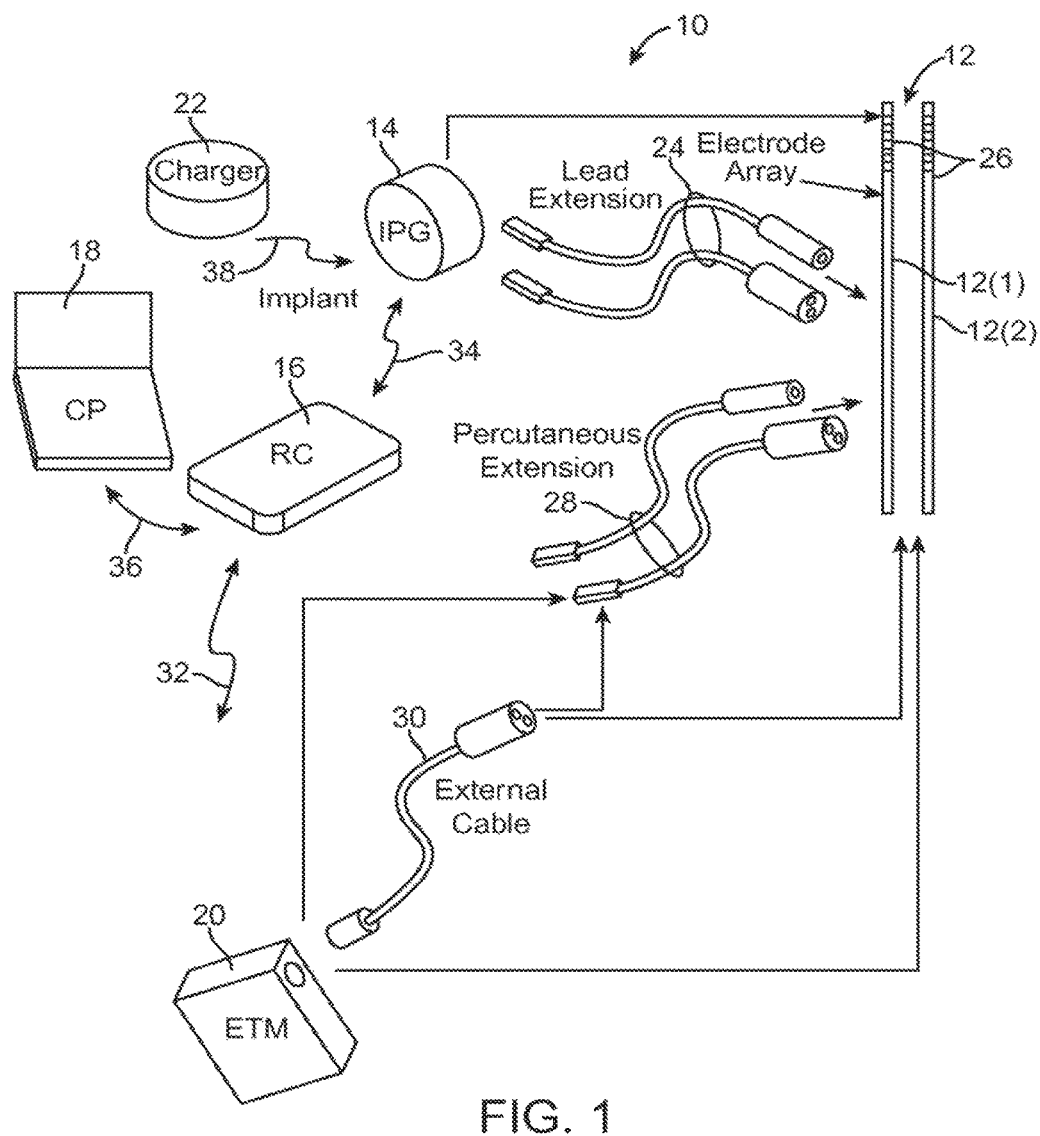
FIG. 1 is plan view of one embodiment of a spinal column modulation (SCM) system arranged in accordance with the present inventions.

Turning first to FIG. 1, an exemplary SCM system 10 generally includes one or more (in this case, two) implantable modulation leads 12(1) and 12(2), a fully implantable modulator (IPG) 14, an external remote controller RC 16, a clinician's programmer (CP) 18, an External Trial Modulator (ETM) 20, and an external charger 22.

The IPG 14 is physically connected via one or more percutaneous lead extensions 24 to the modulation leads 12, which carry a plurality of electrodes 26 arranged in an array. In the illustrated embodiment, the modulation leads 12 are percutaneous leads, and to this end, the electrodes 26 are arranged in-line along the modulation leads 12. In alternative embodiments, the electrodes 26 may be arranged in a two-dimensional pattern on a single paddle lead. As will be described in further detail below, the IPG 14 includes pulse generation circuitry that delivers the electrical modulation energy in the form of an electrical pulse train to the electrode array 26 in accordance with a set of modulation parameters.

The ETM 20 may also be physically connected via the percutaneous lead extensions 28 and external cable 30 to the modulation leads 12. The ETM 20, which has similar pulse generation circuitry as the IPG 14, also delivers electrical modulation energy in the form of an electrical pulse train to the electrode array 26. The major difference between the ETM 20 and the IPG 14 is that the ETM 20 is a non-implantable device that is used on a trial basis after the modulation leads 12 have been implanted and prior to implantation of the IPG 14, to test the responsiveness of the modulation that is to be provided. Thus, any functions described herein with respect to the IPG 14 can likewise be performed with respect to the ETM 20. Further details of an exemplary ETM are described in U.S. Pat. No. 6,895,280, which is expressly incorporated herein by reference.

The RC 16 may be used to telemetrically control the ETM 20 via a hi-directional RF communications link 32. Once the IPG 14 and modulation leads 12 are implanted, the RC 16 may be used to telemetrically control the IPG 14 via a hi-directional RIF communications link 34. Such control allows the IPG 14 to be turned on or off and to be programmed with different modulation parameter sets. The IPG 14 may also be operated to modify the programmed modulation parameters to actively control the characteristics of the electrical modulation energy output by the IPG 14. The CP 18 provides clinician detailed modulation parameters for programming the IPG 14 and ETM 20 in the operating room and in follow-up sessions. The CP 18 may perform this function by indirectly communicating with the IPG 14 or ETM 20, through the RC 16, via an IR communications link 36. Alternatively, the CP 18 may directly communicate with the IPG 14 or ETM 20 via an RF communications link (not shown).

The external charger 22 is a portable device used to transcutaneously charge the IPG 14 via an inductive link 38. For purposes of brevity, the details of the external charger 22 will not be described herein. Details of exemplary embodiments of external chargers are disclosed in U.S. Pat. No. 6,895,280, which has been previously incorporated herein by reference. Once the IPG 14 has been programmed, and its power source has been charged by the external charger 22 or otherwise replenished, the IPG 14 may function as programmed without the RC 16 or CP 18 being present.

Figure 2:
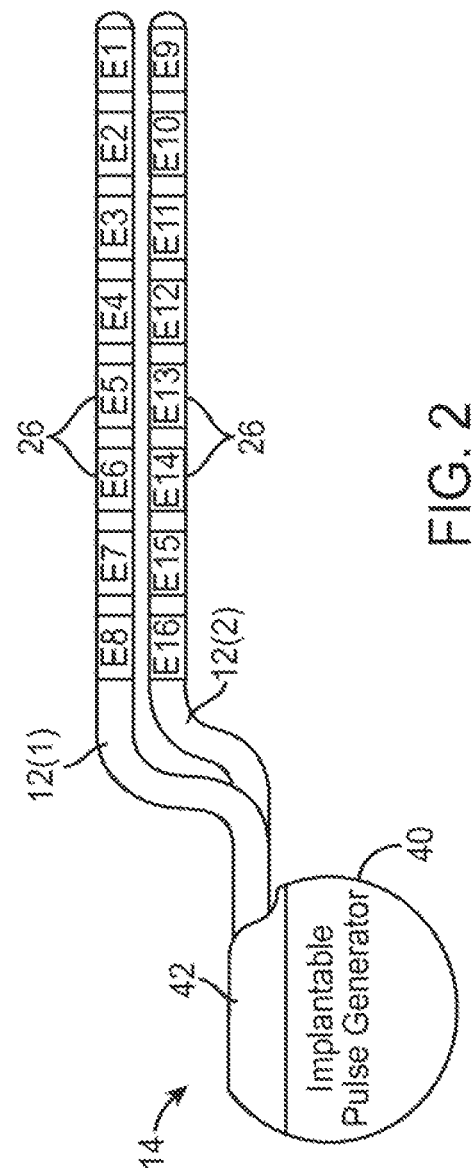
FIG. 2 is a profile view of an implantable pulse generator (IPG) used in the SCM system of FIG. 1.

Referring now to FIG. 2, the external features of the modulation leads 12 and the IPG 14 will be briefly described. One of the modulation leads 12(1) has eight electrodes 26 (labeled E1-E8), and the other modulation lead 12(2) has eight electrodes 26 (labeled E9-E16). The actual number and shape of leads and electrodes will, of course, vary according to the intended application. The IPG 14 comprises an outer case 40 for housing the electronic and other components (described in further detail below), and a connector 42 to which the proximal ends of the modulation leads 12 mate in a manner that electrically couples the electrodes 26 to the electronics within the outer case 40. The outer case 40 is composed of an electrically conductive, biocompatible material, such as titanium, and forms a hermetically sealed compartment wherein the internal electronics are protected from the body tissue and fluids. In some cases, the outer case 40 may serve as an electrode.

As will be described in further detail below, the IPG 14 includes pulse generation circuitry that provides electrical modulation energy to the electrodes 26 in accordance with a. set of modulation parameters. Such parameters may comprise electrode combinations, which define the electrodes that are activated as anodes (positive), cathodes (negative), and turned off zero), and electrical pulse parameters, which define the pulse amplitude (measured in milliamps or volts depending on whether the IPG 14 supplies constant current or constant voltage to the electrodes), pulse width (measured in microseconds), pulse rate (measured in pulses per second), duty cycle (pulse width divided by cycle duration), burst rate (measured as the modulation energy on duration X and modulation energy off duration Y), and pulse shape.

With respect to the pulse patterns provided during operation of the SCM system 10, electrodes that are selected to transmit or receive electrical energy are referred to herein as "activated," while electrodes that are not selected to transmit or receive electrical energy are referred to herein as "non-activated." Electrical energy delivery will occur between two (or more) electrodes, one of which may be the IPG case 40, so that the electrical current has a path from the energy source contained within the IPG case 40 to the tissue and a sink path from the tissue to the energy source contained within the case. Electrical energy may be transmitted to the tissue in a monopolar or multipolar (e.g., bipolar, tripolar, etc.) fashion.

Monopolar delivery occurs when a selected one or more of the lead electrodes 26 is activated along with the case 40 of the IPG 14, so that electrical energy is transmitted between the selected electrode 26 and case 40. Monopolar delivery may also occur when one or more of the lead electrodes 26 are activated along with a large group of lead electrodes located remotely from the one or more lead electrodes 26 so as to create a monopolar effect; that is, electrical energy is conveyed from the one or more lead electrodes 26 in a relatively isotropic manner. Bipolar delivery occurs when two of the lead electrodes 26 are activated as anode and cathode, so that electrical energy is transmitted between the selected electrodes 26. Tripolar delivery occurs when three of the lead electrodes 26 are activated, two as anodes and the remaining one as a cathode, or two as cathodes and the remaining one as an anode.

The electrical energy may be delivered between electrodes as monophasic electrical energy or multiphasic electrical energy. Monophasic electrical energy includes a series of pulses that are either all positive (anodic) or all negative (cathodic). Multiphasic electrical energy includes a series of pulses that alternate between positive and negative. For example, multiphasic electrical energy may include a series of biphasic pulses, with each biphasic pulse including a cathodic (negative) modulation pulse and an anodic (positive) recharge pulse that is generated after the modulation pulse to prevent direct current charge transfer through the tissue, thereby avoiding electrode degradation and cell trauma.

That is, charge is conveyed through the electrode-tissue interface via current at an electrode during a modulation period (the length of the modulation pulse), and then pulled back off the electrode-tissue interface via an oppositely polarized current at the same electrode during a recharge period (the length of the recharge pulse). The recharge pulse may be active, in which case, the electrical current is actively conveyed through the electrode via current or voltage sources, or the recharge pulse may be passive, in which case, the electrical current may be passively conveyed through the electrode via redistribution of the charge flowing from coupling capacitances present in the circuit.

Figure 3:
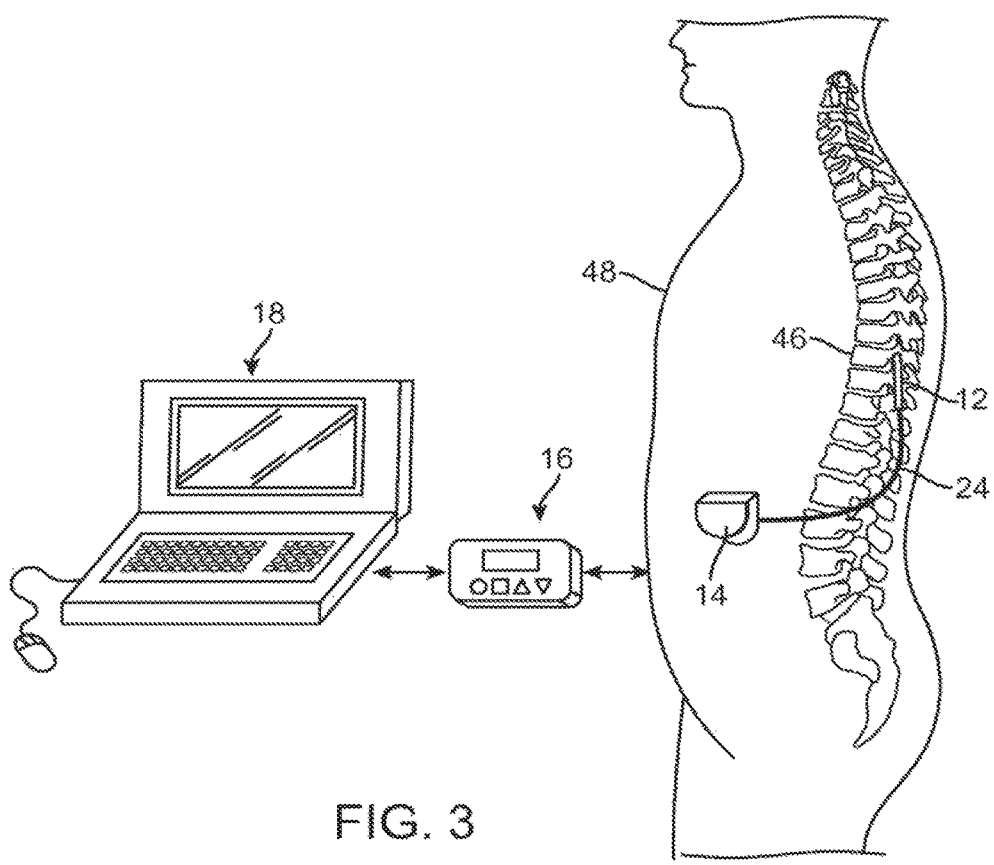
FIG. 3 is a plan view of the SCM system of FIG. 1 in use with a patient.

As shown in FIG. 3, the modulation leads 12 are implanted within the spinal column 46 of a patient 48. The preferred placement of the stimulation leads 12 is adjacent, i.e., resting near, or upon the dura, adjacent to the spinal cord area to be stimulated. The modulation leads 12 will be located in a vertebral position that depends upon the location and distribution of the chronic pain. For example, if the chronic pain is in the lower back or legs, the modulation leads 12 may be located in the mid- to low-thoracic region (e.g., at the T9-12 vertebral levels). Due to the lack of space near the location where the electrode leads 12 exit the spinal column 46, the IPG 14 is generally implanted in a surgically-made pocket either in the abdomen or above the buttocks. The IPG 14 may, of course, also be implanted in other locations of the patient's body. The lead extensions 24 facilitate locating the IPG 14 away from the exit point of the electrode leads 12. As there shown, the CP 18 communicates with the IPG 14 via the RC 16.

Significantly, the SCM system 10 uses feedback indicating the therapeutic effect of electrical modulation energy delivered by the IPG 14 to adjust the delivered electrical modulation energy in a manner that minimizes the energy consumption required by the IPG 14 to generate the electrical modulation energy while providing efficacious therapy. The SCM system 10 may perform this automatically, e.g., in response to a user prompt or periodically (e.g., once a day). In this manner, the electrical modulation energy may be delivered using a modulation parameter that positively impacts battery life and/or recharge interval.

To this end, the SCM system 10 may automatically vary a modulation parameter value by a step size. In this preferred embodiment, this modulation parameter is a pulse rate, which may be, e.g., 2 Hz-100 KHz. However, the present invention lends itself well to relatively high frequency pulse rates (e.g., in the range of 1 KHz-50 KHz, and more preferably in the range of 3 KHz-15 KHz), which require a relatively high energy consumption by the IPG 14, and therefore benefit the most by the minimization of the energy consumption. Other types of modulation parameters that can be used are pulse amplitude, pulse width, and pulse duty cycle. In general, the greater the values of the pulse rate, pulse amplitude, pulse width, and pulse duty cycle, the greater the energy consumption required to generate the electrical energy in accordance with these modulation parameter values.

Another type of modulation parameter is the electrode combination. Notably, the spacing between the cathode(s) and anode(s) used to deliver the electrical energy may dictate the energy consumption required to generate the electrical energy. For example, if the spacing between the cathode(s) and anode(s) is relatively small, there may be substantial shunting of electrical current between the cathode(s) and anode(s), thereby requiring a higher energy consumption in the EPG 14. In contrast, if the spacing between the cathode(s) and anode(s) is relatively great, there may be insubstantial shunting of electrical current between the cathode(s) and anode(s), thereby requiring a lower energy consumption in the IPG 14. Thus, the greater the spacing between the cathode(s) and anode(s), the lesser the energy consumption required to generate the electrical energy in accordance with this modulation parameter value.

The step size by which the modulation parameter value is varied may depend on the nature of the modulation parameter value, as well as the accuracy of the desired resolution of the energy consumption minimization/processing time. For example, if the stimulation parameter is a pulse rate, the step size may be 1000 Hz, although the step size may be decreased to, e.g., 500 Hz, if more accuracy in the resolution of the energy consumption minimization is desired, or may be increased to, e.g., 2000 Hz if a quicker processing time is desired. As another example, if the stimulation parameter is a pulse amplitude, the step size may be 0.1 mA. If the stimulation parameter is a pulse width, the step size may be 10 μs. If the stimulation parameter is a pulse duty cycle, the step size may be 10%. If the stimulation parameter is an electrode combination, the step size may be the electrode spacing of the modulation lead, e.g., 5 mm.

The SCM system 10 may instruct the IPG 14 to output the electrical energy to electrodes 26 in accordance with a varied modulation parameter value, and in response to this, comparing a therapeutic feedback indicator to a threshold stored in the SCM system 10. The therapeutic feedback indicator can be any feedback that indicates the level of the therapeutic effect on the patient in response to the delivery of the electrical modulation energy. For example, the therapeutic feedback indicator can be subjective conscious feedback provided by the patient, e.g., verbal or written feedback, which can, in turn, be entered into the SCM system 10. The therapeutic feedback indicator may alternatively be objective and measured, e.g., using one or more sensors. In this case, the therapeutic feedback indicator maybe, e.g., a body activity (measured using accelerometer or electrode impedance variation), body temperature, blood flow (peripheral or central), electrocardiogram and derived autonomic tone metrics thereof, electrocortigram, electroencephalogram, tissue or transcutaneous oxygen tension, glucose concentration, electrode impedance, compound action potentials, intra- or extra-cellular potential or electrical current, and chemical species concentration (intrathecally, epidurally, or subcutaneously).

Based on the comparison between the therapeutic feedback indicator to the stored threshold, the SCM system 10 determines whether the therapeutic goal has been met. For example, if the therapeutic goal is the alleviation of at least fifty percent of the chronic pain, and the therapeutic feedback indicator is subjective conscious feedback from the patient, the therapeutic goal can be determined to be met if the patient indicates that at least fifty percent of the chronic pain has been alleviated by the delivered electrical modulation energy, and not met if the patient indicates that less than fifty percent of the chronic pain has been alleviated by the delivered electrical modulation energy. If the therapeutic feedback indicator is an objective measurement, the measured indicator value may simply be compared to a corresponding threshold value to determine whether the therapeutic goal has been met.

The SCM system 10 repeats the foregoing steps to determine the modulation parameter value at the resolution of the step size that minimizes energy consumption of the IPG 14 required to meet the therapeutic goal when delivering the electrical energy to the electrodes 26 in accordance with the varied modulation parameter value. This determination may be accomplished using one of two techniques.

In the first technique, the therapeutic goal is not met on the initial conveyance of the electrical energy to the electrodes 26 and the energy consumption of the IPG 14 is gradually increased until the therapeutic goal is met. In particular, the SCM system 10 repeats the modulation parameter value varying, electrical energy conveyance, therapeutic feedback comparison, and therapeutic goal determination steps until the therapeutic goal is met. In this case, the modulation parameter value that minimizes energy consumption of the IPG 14 required to meet the therapeutic goal is determined to be the last modulation parameter value used by the SCM system 10. The electrical energy can be conveyed from the IPG 14 to the electrodes 26 in accordance with this modulation parameter value to provide the therapy until another adjustment is needed.

In the second technique, the therapeutic goal is met on the initial conveyance of the electrical energy to the electrodes 26 and the energy consumption of the IPG 14 is gradually decreased until the therapeutic goal is not met. In particular, the SCM system 10 repeats the modulation parameter value varying, electrical energy conveyance, therapeutic feedback comparison, and therapeutic goal determination steps until the therapeutic goal is not met. In this case, the modulation parameter value that minimizes energy consumption of the IPG 14 required to meet the therapeutic goal is determined to be the last modulation parameter value used by the SCM system 10 that met the therapeutic goal. In this case, the current modulation parameter value can be incremented onestep back to the previous modulation parameter value to increase the energy consumption of the IPG 14, and the electrical energy can be conveyed from the IPG 14 to the electrodes 26 in accordance with this modulation parameter value to provide the therapy until another adjustment is needed.

As will be described in further detail below, either or both of the memory that stores the threshold, and the controller/processor that performs the functions of these techniques, can be contained either in the IPG 14 or the RC 16, or even the CP 18. The optional sensor can be carried by the IPG 14, the modulation leads 12, or can be separate from these devices. Although only one therapeutic feedback indicator is described as being compared to a single threshold, multiple therapeutic feedback indicators may be separately compared to multiple thresholds or can be used in combination and compared to a single threshold. The therapeutic feedback indicator or indicators may be weighted by linear or non-linear functions. Any thresholds or calibration of variables involved with the feedback loop may be calibrated at a clinic before the patient is sent home. Optionally, the SCM system 10 may be placed into a "learning mode" that captures input from a patient while tracking all or selected therapeutic feedback indicators, and from these indicators, the most representative and sensitive indicators may be chosen to provide feedback to the energy consumption minimization technique.

Figure 4:
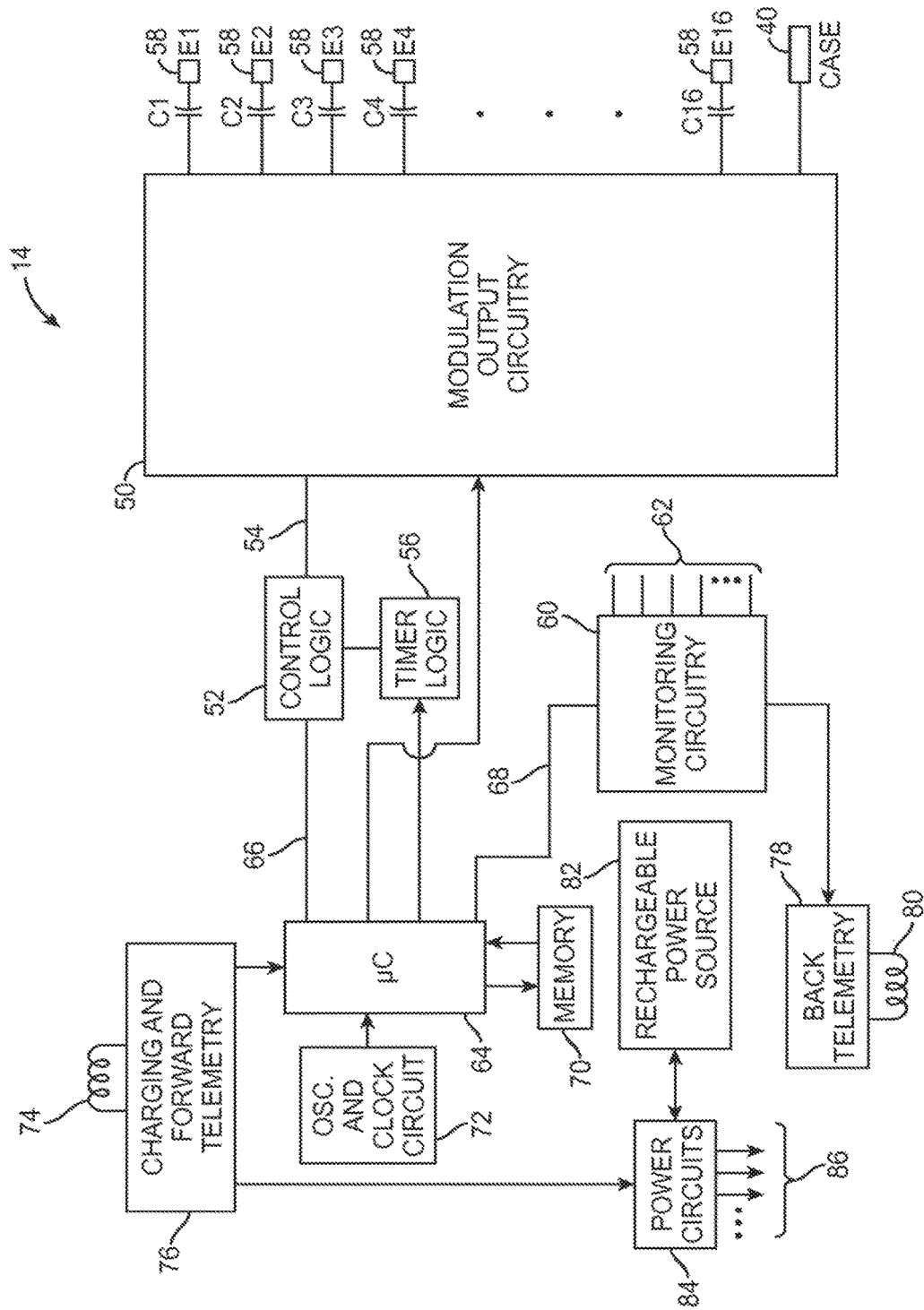
FIG. 4 is a block diagram of the internal components of the IPG of FIG. 2.

Turning next to FIG. 4, one exemplary embodiment of the IPG 14 will now be described. The IPG 14 includes modulation output circuitry 50 configured for generating electrical modulation energy in accordance with an electrical pulse train having a specified pulse amplitude, pulse rate, pulse width, duty cycle, burst rate, and shape under control of control logic 52 over data bus 54. Control of the pulse rate and duration is facilitated by analog circuitry, or digital timer logic circuitry 56 controlling the analog circuitry, and which may have a suitable resolution, e.g., 10 μs. In alternative embodiments, a continuous modulating waveform may be generated by the modulation output circuitry 50 in a manner described in U.S. Provisional Patent Application Ser. No. 61/646,773, entitled "System and Method for Shaped Phased Current Delivery," (corresponding to U.S. patent application Ser. No. 13/893,094, published as US 20130304152 A1, now abandoned) which is expressly incorporated herein by reference. The modulation energy generated by the modulation output circuitry 50 is output via capacitors C1-C16 to electrical terminals 58 corresponding to electrodes E1-E16.

The modulation output circuitry 50 may either comprise independently controlled current sources for providing stimulation pulses of a specified and known amperage to or from the electrical terminals 58, or independently controlled voltage sources for providing stimulation pulses of a specified and known voltage at the electrical terminals 58 or to multiplexed current or voltage sources that are then connected to the electrical terminals 58. The operation of this modulation output circuitry, including alternative embodiments of suitable output circuitry for performing the same function of generating stimulation pulses of a prescribed amplitude and width, is described more fully in U.S. Pat. Nos. 6,516,227 and 6,993,384, which are expressly incorporated herein by reference.

The IPG 14 also comprises monitoring circuitry 60 for monitoring the status of various nodes or other points 62 throughout the IPG 14, e.g., power supply voltages, temperature, battery voltage, and the like. To the extent that the previously discussed therapeutic feedback indicator is objective and is measured, the monitoring circuitry 60 can monitor these indicators using one or more sensors. The characteristics of the sensor(s) will depend on the nature of the therapeutic feedback indicator to be measured. For example, if the indicators are electrical measurements, the sensors may be the electrodes 26. Otherwise, separate sensors (not shown) may used to take the non-electrical measurements. Of course, if the subject conscious feedback from the patient is used, no sensors are required.

The IPG 14 further comprises processing circuitry in the form of a microcontroller (μC) 64 that controls the control logic 52 over data bus 66, and obtains status data from the monitoring circuitry 60 via data bus 68. The IPG 14 additionally controls the timer logic 56. The IPG 14 further comprises memory 70 and oscillator and clock circuit 72 coupled to the microcontroller 64. The microcontroller 64, in combination with the memory 70 and oscillator and clock circuit 72, thus comprise a microprocessor system that carries out a program function in accordance with a suitable program stored in the memory 70. Alternatively, for some applications, the function provided by the microprocessor system may be carried out by a suitable state machine.

Thus, the microcontroller 64 generates the necessary control and status signals, which allow the microcontroller 64 to control the operation of the IPG 14 in accordance with a selected operating program and modulation parameters. In controlling the operation of the IPG 14, the microcontroller 64 is able to individually generate electrical energy at the electrodes 26 using the modulation output circuitry 50, in combination with the control logic 52 and timer logic 56, thereby allowing each electrode 26 to be paired or grouped with other electrodes 26, including the monopolar case electrode, to control the polarity, pulse amplitude, pulse rate, pulse width, and pulse duty cycle through which the electrical energy is provided.

The IPG 14 further comprises an alternating current (AC) receiving coil 74 for receiving programming data (e.g., the operating program and/or modulation parameters) from the RC 16 and/or CP 18 in an appropriate modulated carrier signal, and charging and forward telemetry circuitry 76 for demodulating the carrier signal it receives through the AC receiving coil 74 to recover the programming data, which programming data is then stored within the memory 70, or within other memory elements (not shown) distributed throughout the IPG 14.

The IPG 14 further comprises back telemetry circuitry 78 and an alternating current (AC) transmission coil 80 for sending informational data sensed through the monitoring circuitry 60 to the RC 16 and/or CP 18. The back telemetry features of the IPG 14 also allow its status to be checked. For example, when the RC 16 and/or CP 18 initiates a programming session with the IPG 14, the capacity of the battery is telemetered, so that the RC 16 and/or CP 18 can calculate the estimated time to recharge. Any changes made to the current stimulus parameters are confirmed through back telemetry, thereby assuring that such changes have been correctly received and implemented within the implant system. Moreover, upon interrogation by the RC 16 and/or CP 18, all programmable settings stored within the IPG 14 may be uploaded to the RC 16 and/or CP 18.

Notably, to the extent that the microcontroller 64 is used to perform the control/processing functions of the energy consumption minimization techniques described above, the therapeutic feedback indicators, to the extent that they are objectively measured, can be obtained from the monitoring circuitry 60, and the threshold to which the therapeutic feedback indicators are compared can be stored and recalled from the memory 70. To the extent that the therapeutic feedback indicators are entered into the RC 16 or the CP 18 (e.g., if the therapeutic feedback indicators are conscious feedback parameters), these feedback indicators can be received from the RC 16 or CP 18 via the coil 74 and forward telemetry circuitry 76. In contrast, if the RC 16, or alternatively the CP 18, is used to perform the control/processing function of the energy consumption minimization techniques described above, the therapeutic feedback indicators, to the extent that they are objectively measured by sensor(s) coupled to the IPG 14, can be transmitted from the IPG 14 to the RC 16 or CP 18 via the back telemetry circuitry 78 and coil 80.

The IPG 14 further comprises a rechargeable power source 82 and power circuits 84 for providing the operating power to the IPG 14. The rechargeable power source 82 may, comprise a lithium-ion or lithium-ion polymer battery. The rechargeable battery 82 provides an unregulated voltage to the power circuits 84. The power circuits 84, in turn, generate the various voltages 86, some of which are regulated and some of which are not, as needed by the various circuits located within the IPG 14. The rechargeable power source 8 is recharged using rectified AC power (or DC power converted from AC power through other means, e.g., efficient AC-to-DC converter circuits, also known as "inverter circuits") received by the AC receiving coil 74. To recharge the power source 82, an external charger (not shown), which generates the AC magnetic field, is placed against, or otherwise adjacent, to the patient's skin over the implanted IPG 14. The AC magnetic field emitted by the external charger induces AC currents in the AC receiving coil 74. The charging and forward telemetry circuitry 76 rectifies the AC current to produce DC current, which is used to charge the power source 82. While the AC receiving coil 74 is described as being used for both wirelessly receiving communications e.g., programming and control data) and charging energy from the external device, it should be appreciated that the AC receiving coil 74 can be arranged as a dedicated charging coil, while another coil, such as coil 80, can be used for bi-directional telemetry.

Additional details concerning the above-described and other IPGs may be found in U.S. Pat. No. 6,516,227, U.S. Patent Publication No. 2003/0139781, now issued as U.S. Pat. No. 6,993,384, and U.S. patent application Ser. No. 11/138,632, entitled "Low Power Loss Current Digital-to-Analog Converter Used in an Implantable Pulse Generator," now issued as U.S. Pat. No. 7,539,538, which are expressly incorporated herein by reference. It should be noted that rather than an IPG, the SCM system 10 may alternatively utilize an implantable receiver-stimulator (not shown) connected to leads 12. In this case, the power source, e.g., a battery, for powering the implanted receiver, as well as control circuitry to command the receiver-stimulator, will be contained in an external controller inductively coupled to the receiver-stimulator via an electromagnetic link. Data/power signals are transcutaneously coupled from a cable-connected transmission coil placed over the implanted receiver-stimulator. The implanted receiver-stimulator receives the signal and generates the modulation in accordance with the control signals.

Figure 5:
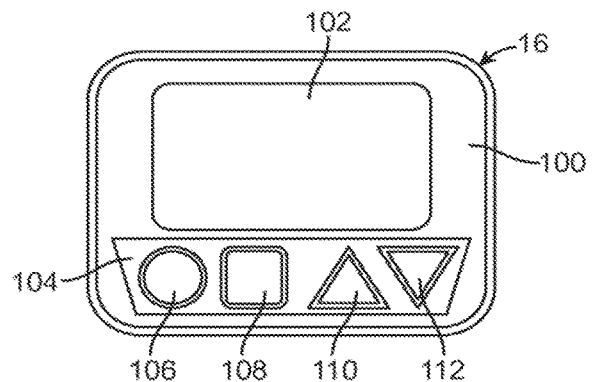
FIG. 5 is a plan view of a hand-held remote control (RC) that can be used in the SCM system of FIG. 1.

Referring now to FIG. 5, one exemplary embodiment of an RC 16 will now be described. As previously discussed, the RC 16 is capable of communicating with the IPG 14, CP 18, or ETM 20. The RC 16 comprises a casing 100, which houses internal componentry (including a printed circuit board (PCB)), and a lighted display screen 102 and button pad 104 carried by the exterior of the casing 100. In the illustrated embodiment, the display screen 102 is a lighted flat panel display screen, and the button pad 104 comprises a membrane switch with metal domes positioned over a flex circuit, and a keypad connector connected directly to a PCB. In an optional embodiment, the display screen 102 has touchscreen capabilities. The button pad 104 includes a multitude of buttons 106, 108, 110, and 112, which allow the IPG 14 to be turned ON and OFF, provide for the adjustment or setting of modulation parameters within the IPG 14, and provide for selection between screens.

In the illustrated embodiment, the button 106 serves as an ON/OFF button that can be actuated to turn the IPG 14 ON and OFF. The button 108 serves as a select button that allows the RC 106 to switch between screen displays and/or parameters. The buttons 110 and 112 serve as up/down buttons that can be actuated to increase or decrease any of modulation parameters of the pulse generated by the IPG 14, including the pulse amplitude, pulse width, and pulse rate. For example, the selection button 108 can be actuated to place the RC 16 in a "Pulse Amplitude Adjustment Mode," during which the pulse amplitude can be adjusted via the up/down buttons 110, 112, a "Pulse Width Adjustment Mode," during which the puke width can be adjusted via the up/down buttons 110, 112, and a "Pulse Rate Adjustment Mode," during which the pulse rate can be adjusted via the up/down buttons 110, 112. Alternatively, dedicated up/down buttons can be provided for each stimulation parameter. Rather than using up/down buttons, any other type of actuator, such as a dial, slider bar, or keypad, can be used to increment or decrement the stimulation parameters.

Figure 6:
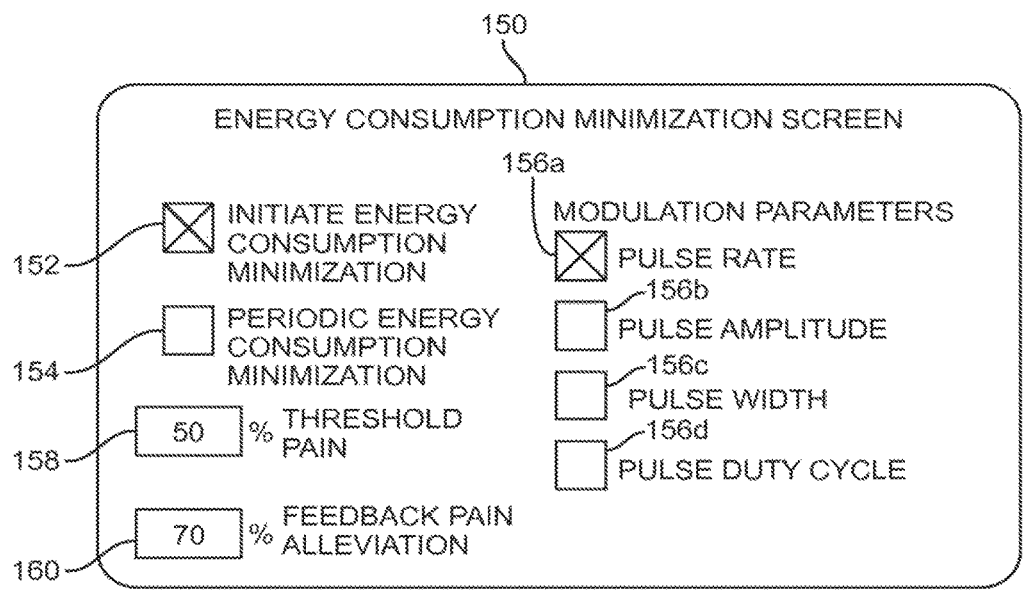
FIG. 6 is a plan view of a display screen generated by the RC of FIG. 5 to provide a means for the energy consumption of the IPG of FIG. 2.

Significant to the present inventions, the selection button 108 can also be actuated to place the RC 16 in an "Energy Minimization" mode that calibrates a selected modulation parameter that minimizes the energy consumption of the IPG 14 when delivering the therapeutic electrical energy, as discussed above. For example, FIG. 6 illustrates a programming screen 150 that includes an energy consumption minimization trigger box 152 that can be checked to initiate a process for minimizing the energy consumption of the IPG 14, Alternatively, the IPG 14 by itself, or the RC 16 may periodically initiate the energy consumption minimization process without user intervention. In this case, the programming screen 150 may include an ON/OFT check box 154 that can be checked to turn this feature on and unchecked to turn this feature off. When on, the IPG 14 or RC 16 will periodically initiate the energy consumption minimization process. When off, the IPG 14 or RC 16 will never initiate the energy consumption minimization process.

The programming screen 150 also has a list of modulation parameters and associated check boxes 156 that can be actuated to select the modulation parameter that is to be varied to minimize the energy consumption of the IPG 14. For example, the puke rate can be selected by checking box 156a, the pulse amplitude can be selected by checking box 156b, the pulse width can be selected by checking box 156c, and the pulse duty cycle can be selected by checking box 156d. The programming screen 150 further includes a threshold entry box 158 in which a threshold value to which the therapeutic feedback indicator will be compared. For example, if the therapeutic feedback indicator is a percentage of chronic pain that has been alleviates in accordance with subjective feedback from the patient, a percentage (e.g., 50% can be input into the box 156). If the therapeutic feedback indicators are objective measurements, the corresponding threshold can be input into the box 158. In the case where the therapeutic feedback indicator is subjective conscious feedback from the patient, the programming screen 150 further includes a patient feedback box 160 in which the user may input the therapeutic effect of the electrical stimulation as a percentage of pain alleviated.

Figure 7:
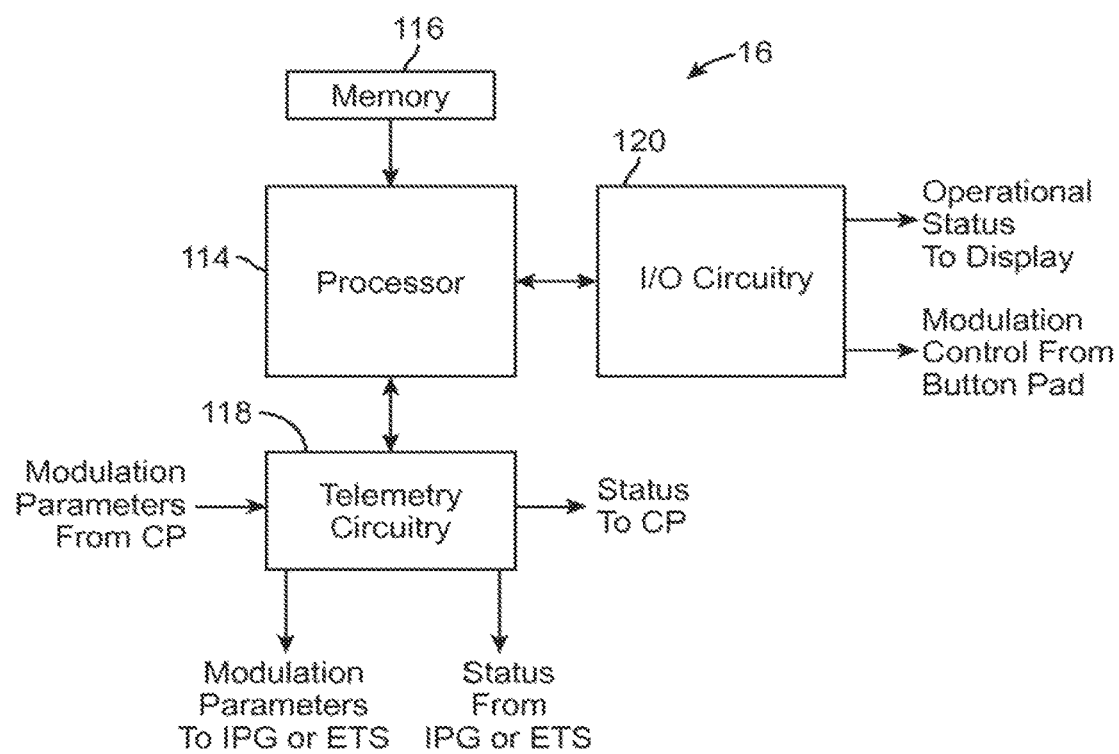
FIG. 7 is a block diagram of the internal components of the RC of FIG. 5.

Referring to FIG. 7, the internal components of an exemplary RC 16 will now be described. The RC 16 generally includes a processor 114 (e.g., a microcontroller), memory 116 that stores an operating program for execution by the processor 114, as well as modulation parameters, input/output circuitry, and in particular, telemetry circuitry 118 for outputting modulation parameters to the IPG14 and receiving status information from the IPG 14, and input/output circuitry 120 for receiving modulation control signals from the button pad 104 and transmitting status information to the display screen 102 (shown in FIG. 5). As well as controlling other functions of the RC 16, which will not be described herein for purposes of brevity, the processor 114 generates a plurality of modulation parameter sets that define the amplitude, phase duration, frequency, and waveform shape in response to the user operation of the button pad 104. These new modulation parameter sets would then be transmitted to the IPG 14 via the telemetry circuitry 118, thereby adjusting the modulation parameters stored in the IPG 14 and/or programming the IPG 14. The telemetry circuitry 118 can also be used to receive modulation parameters from the CP 18. Notably, to the extent that the processor 114 is used to perform the control/processing, functions of the energy consumption minimization techniques described above, the therapeutic feedback indicators, to the extent that they are objectively measured, can be received from the IPG 14 via the telemetry circuitry 118. Further details of the functionality and internal componentry of the RC 16 are disclosed in U.S. Pat. No. 6,895,280, which has previously been incorporated herein by reference.

Although the foregoing programming functions have been described as being at least partially implemented in the RC 16, it should be noted that these techniques may be at least, in part, be alternatively or additionally implemented in the CP 18.

Figure 8:
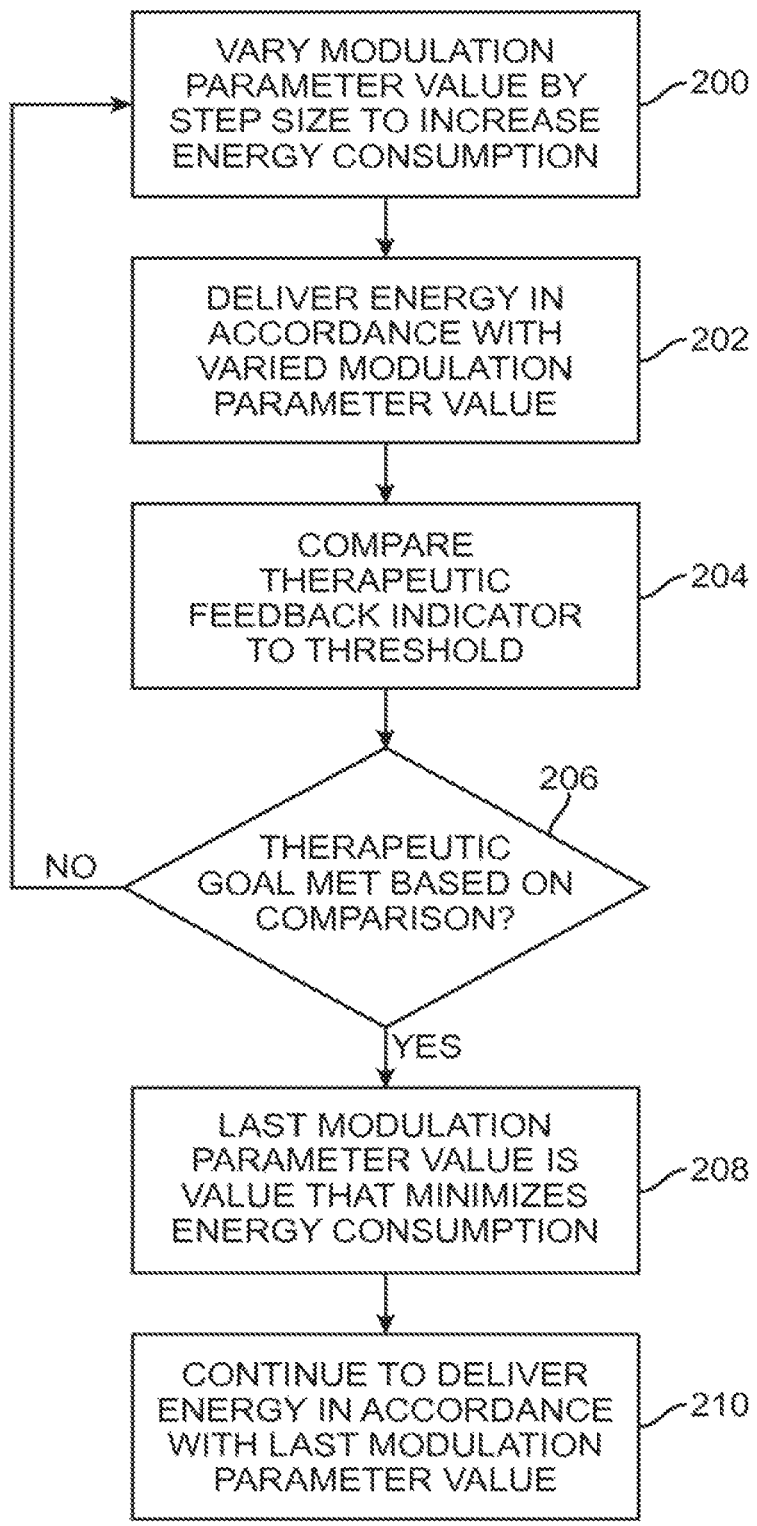
FIG. 8 is a flow diagram illustrating one technique used by the SCM system to minimize the energy consumption in the IPG of FIG. 2.

Having described the structure and function of the SCM system 10, one technique for operating the system 10 to minimize the energy consumption of the IPG 14 while providing efficacious therapy will now be described with reference to FIG. 8. This technique assumes that the therapeutic goal is not initially met when electrical energy is delivered from the IPG 14 to the electrodes 26 in accordance with a modulation parameter value.

First, the modulation parameter value is incrementally varied by a step size, and in particular, varied in a manner that increases the energy consumption of the IPG 14 (step 200). Then, electrical energy is delivered from the IPG 14 to the electrodes 26 in accordance with the varied modulation parameter value, thereby modulating a target tissue site step 202). Next, a therapeutic feedback indicator is analyzed in response to the modulation of the target tissue site by the delivered electrical energy. In particular, a threshold is recalled from memory, and the therapeutic feedback indicator is compared to the recalled threshold (step 204). As previously discussed, the therapeutic feedback indicator can be subjective conscious feedback from the patient that is subsequently entered into the RC 16 or CP 18, or the therapeutic feedback indicator can be an objective measurement taken by the IPG 14. Then, it is determined whether the therapeutic goal has been met based on the comparison (step 206).

Next, steps 200-206 are repeated to determine the modulation parameter value at the resolution of the step size that minimizes energy consumption of the IPG 14 required to meet the therapeutic goal when delivering the electrical energy to the electrodes 26 in accordance with the varied modulation parameter value. In particular, if the therapeutic goal has been determined to not be met at step 206, then steps 200-206 are repeated. If the therapeutic goal has been determined to be met at step 206, the modulation parameter value that minimizes energy consumption of the IPG 14 required to meet the therapeutic goal is determined to be the last modulation parameter value (step 208). Electrical energy continues to be delivered from the IPG 14 to the electrodes 26 in accordance with this last modulation parameter value, thereby modulating a target tissue site (step 210), until the energy consumption minimization technique is initiated again.

Figure 9:
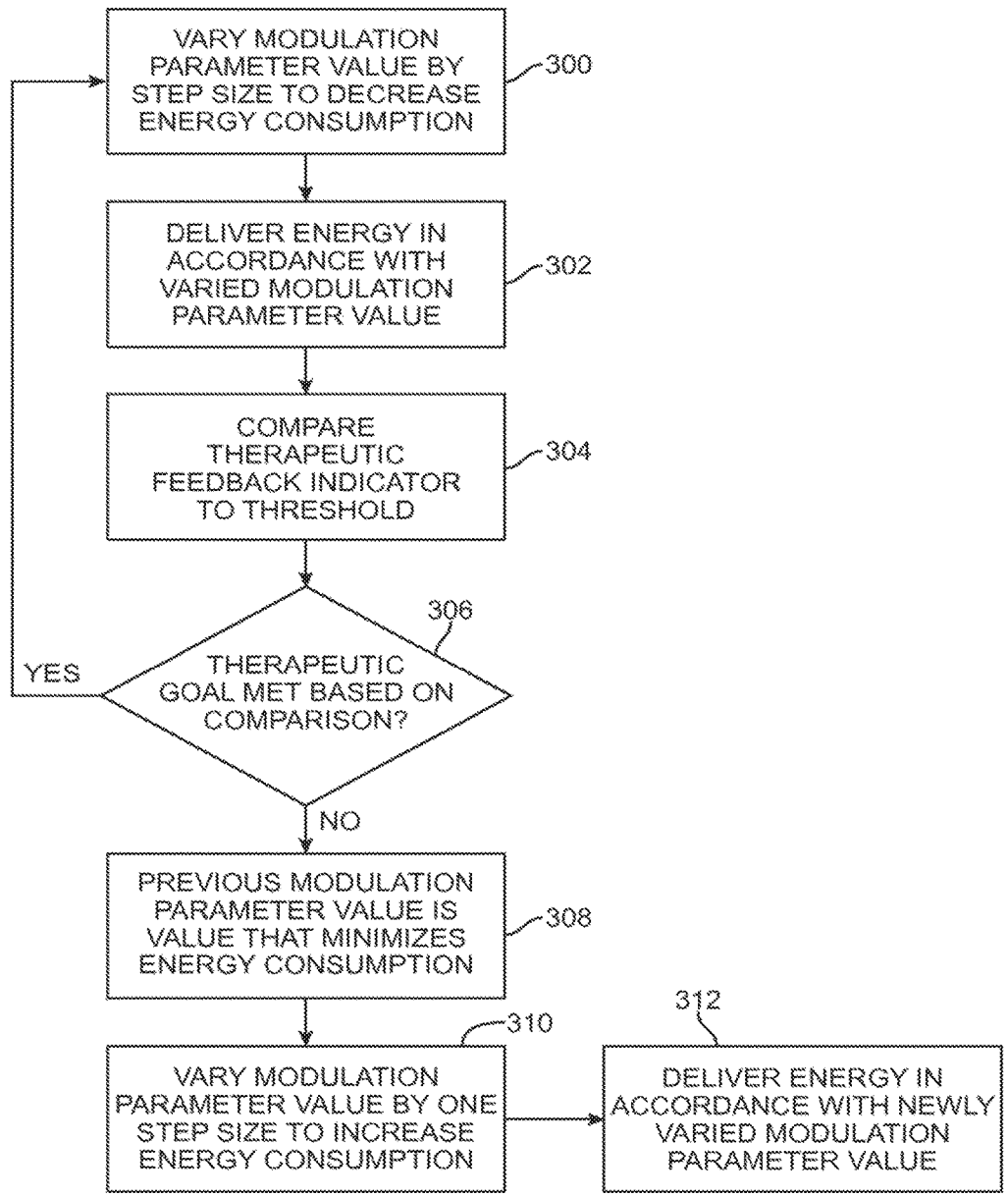
FIG. 9 is a flow diagram illustrating another technique used by the SCM system to minimize the energy consumption in the IPG of FIG. 2.

Another technique for operating the system 10 to minimize the energy consumption of the IPG 14 while providing efficacious therapy will now be described with reference to FIG. 9. This technique assumes that the therapeutic goal is initially met when electrical energy is delivered from the IPG 14 to the electrodes 26 in accordance with a modulation parameter value.

First, the modulation parameter value is incrementally varied by a step size, and in particular, varied in a manner that decreases the energy consumption of the IPG 14 (step 300). Then, electrical energy is delivered from the IPG 14 to the electrodes 26 in accordance with the varied modulation parameter value, thereby modulating a target tissue site step 302). Next, a therapeutic feedback indicator is analyzed in response to the modulation of the target tissue site by the delivered electrical energy. In particular, a threshold is recalled from memory, and the therapeutic feedback indicator is compared to the recalled threshold (step 304). As just discussed, the therapeutic feedback indicator can be subjective conscious feedback from the patient that is subsequently entered into the RC 16 or CP 18, or the therapeutic feedback indicator can be an objective measurement taken by the IPG 14. Then, it is determined whether the therapeutic goal has been met based on the comparison (step 306).

Next, steps 300-306 are repeated to determine the modulation parameter value at the resolution of the step size that minimizes energy consumption of the IPG 14 required to meet the therapeutic goal when delivering the electrical energy to the electrodes 26 in accordance with the varied modulation parameter value. In particular, if the therapeutic goal has been determined to be met at step 306, then steps 300-306 are repeated. If the therapeutic goal has been determined to be not met at step 306, the modulation parameter value that minimizes energy consumption of the IPG 14 required to meet the therapeutic goal is determined to be the previous modulation parameter value (step 308). In this case, the modulation parameter value is varied by one step size in a manner that increases the energy consumption of the IPG 14 (essentially getting back to the previous modulation parameter value) (step 310). Electrical energy is then delivered from the IPG 14 to the electrodes 26 in accordance with this previous modulation parameter value, thereby modulating a target tissue site step 312), until the energy consumption minimization technique is initiated again.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A method, comprising:
   using a modulation parameter to deliver electrical energy from a neuromodulation device through at least one electrode;
   using a therapeutic feedback indicator to confirm that a therapeutic goal is met by the delivered electrical energy; and
   initiating an automatic process to reduce the electrical energy delivered from the neuromodulation device, wherein the automatic process includes incrementally changing the modulation parameter to reduce the electrical energy, delivering the electrical energy using the incrementally-changed modulation parameter, and using the therapeutic feedback indicator to confirm that the therapeutic goal is met.

2. The method of claim 1, wherein the automatic process further includes automatically repeating the incrementally changing, the delivering, and the using the therapeutic feedback indicator until the therapeutic goal is unmet.

3. The method of claim 1, wherein the electrical energy comprises pulsed electrical energy.

4. The method of claim 1, wherein the modulation parameter comprises a pulse rate.

5. The method of claim 1, wherein the modulation parameter comprises a pulse width.

6. The method of claim 1, wherein the modulation parameter comprises a duty cycle.

7. The method of claim 1, wherein the modulation parameter comprises an amplitude.

8. The method of claim 1, wherein the modulation parameter comprises an electrode combination.

9. The method of claim 1, wherein the using the therapeutic feedback indicator includes using conscious patient feedback.

10. The method of claim 1, wherein the using the therapeutic feedback indicator includes using a signal indicative of at least one of:
    a body activity;
    a body temperature; or
    a blood flow.

11. The method of claim 1, wherein the using the therapeutic feedback indicator includes using a signal indicative of at least one of:
    an electrocardiogram or derived autonomic tone metrics thereof;
    an electrocortigram; or
    an electroencephalogram.

12. The method of claim 1, wherein the using the therapeutic feedback indicator includes using a signal indicative of at least one of:
   a tissue or transcutaneous oxygen tension;
   a glucose concentration; or
   an electrode impedance.

13. The method of claim 1, wherein the using the therapeutic feedback indicator includes using a signal indicative of at least one of:
   compound action potentials;
   an intra- or extra-cellular potential or electrical current; or
   a chemical species concentration.

14. The method of claim 1, wherein the using the therapeutic feedback indicator comprises comparing the therapeutic feedback indicator to a threshold indicative of the therapeutic goal to confirm that the therapeutic goal is met.

15. The method of claim 1, wherein using the therapeutic feedback indicator to confirm that the therapeutic goal is met includes using the therapeutic feedback indicator to confirm alleviation of chronic pain.

16. The method of claim 1, wherein using the modulation parameter to deliver the electrical energy includes using the modulation parameter to deliver the electrical energy from the neuromodulation device through an implantable electrode.

17. A system, comprising:
   delivery means for delivering electrical energy having at least one modulation parameter through at least one electrode; and
   control means for automatically using a therapeutic feedback indicator to confirm that a therapeutic goal is met by the delivered electrical energy, incrementally changing the modulation parameter to reduce the electrical energy, instructing the delivery means to deliver the electrical energy in accordance with the incrementally changed modulation parameter, and using the therapeutic feedback indicator to confirm that the therapeutic goal is met.

18. The system of claim 17, wherein the control means is further configured to automatically repeat the incrementally changing, the instructing, and the using the therapeutic feedback indicator until the therapeutic goal is unmet.

19. A system, comprising:
   a neuromodulation device configured to deliver electrical energy having at least one modulation parameter through at least one electrode; and
   controller circuitry configured to automatically use a therapeutic feedback indicator to confirm that a therapeutic goal is met by the delivered electrical energy, incrementally change the modulation parameter to reduce the electrical energy, instruct the neuromodulation device to deliver the electrical energy in accordance with the incrementally changed modulation parameter, and use the therapeutic feedback indicator to confirm that the therapeutic goal is met.

20. The system of claim 19, wherein the controller circuitry is further configured to automatically and repeatedly incrementally change the modulation parameter to reduce the electrical energy, instruct the neuromodulation device to deliver the electrical energy in accordance with the incrementally changed modulation parameter, and use the therapeutic feedback indicator until the therapeutic goal is unmet.

* * * * *